United States Patent
Imai

(10) Patent No.: US 11,358,483 B2
(45) Date of Patent: Jun. 14, 2022

(54) SERVER, VEHICLE, AND CHARGER INFORMATION METHOD

(71) Applicant: Toyota Jidosha Kabushiki Kaisha, Toyota (JP)

(72) Inventor: Tsutomu Imai, Inazawa (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 325 days.

(21) Appl. No.: 16/578,830

(22) Filed: Sep. 23, 2019

(65) Prior Publication Data

US 2020/0094698 A1  Mar. 26, 2020

(30) Foreign Application Priority Data

Sep. 25, 2018 (JP) .............................. JP2018-178834

(51) Int. Cl.
*B60L 53/30* (2019.01)
*A61B 5/18* (2006.01)
(Continued)

(52) U.S. Cl.
CPC .......... *B60L 53/305* (2019.02); *A61B 5/1103* (2013.01); *A61B 5/1128* (2013.01);
(Continued)

(58) Field of Classification Search
CPC .... B60L 53/305; B60L 2240/72; B60L 53/62; B60W 40/08; B60W 50/14;
(Continued)

(56) References Cited

U.S. PATENT DOCUMENTS 6,014,081 A * 1/2000 Kojima ..................... G07C 5/04
340/439
2008/0291008 A1* 11/2008 Jeon ................... G06K 9/00979
340/539.1
(Continued)

FOREIGN PATENT DOCUMENTS

CN        105365824 A  *  3/2016 ........... B60R 16/023
JP      2012-251989 A    12/2012
(Continued)

OTHER PUBLICATIONS

EPO machine translation of JP 2013-171524 (original JP document published Sep. 2, 2013) (Year: 2013).*
(Continued)

*Primary Examiner* — David A Testardi
(74) *Attorney, Agent, or Firm* — Dinsmore & Shohl LLP

(57) ABSTRACT

A server informs a vehicle of chargers, the vehicle being mounted with a battery. The vehicle includes a fatigue detection device configured to detect a fatigue level of the driver. A server includes a communication device configured to receive information indicative of the fatigue level of the driver from the vehicle, and a processor configured to extract at least one charger from among multiple chargers installed within an access range of the vehicle if the driver's fatigue level is above a given reference value, and inform the vehicle of the extracted charger, the access range being determined by power stored in the battery and the current location of the vehicle.

9 Claims, 11 Drawing Sheets

(51) Int. Cl.
*B60L 53/67* (2019.01)
*B60L 53/62* (2019.01)
*H04W 4/44* (2018.01)
*A61B 5/11* (2006.01)

(52) U.S. Cl.
CPC .............. *A61B 5/18* (2013.01); *B60L 53/62* (2019.02); *B60L 53/67* (2019.02); *H04W 4/44* (2018.02); *B60Y 2200/91* (2013.01); *B60Y 2300/91* (2013.01)

(58) Field of Classification Search
CPC . B60W 2040/0818; B60W 2040/0827; B60W 2050/143; B60R 21/01512; B60K 28/06; G08B 21/06; A61B 5/18; A61B 5/4809; G01C 21/3469; G01C 21/3484; G01C 21/3697
See application file for complete search history.

(56) References Cited

U.S. PATENT DOCUMENTS

| | | | | |
|---|---|---|---|---|
| 2010/0169008 | A1* | 7/2010 | Niwa | B60L 53/305 701/532 |
| 2011/0032110 | A1* | 2/2011 | Taguchi | B60L 3/12 340/636.1 |
| 2012/0290506 | A1* | 11/2012 | Muramatsu | G01C 21/3476 705/412 |
| 2015/0032661 | A1* | 1/2015 | Manfield | B60L 1/02 705/347 |
| 2015/0266379 | A1* | 9/2015 | Bellin | B60L 53/31 701/36 |
| 2016/0033297 | A1* | 2/2016 | Konishi | G06Q 50/30 701/31.4 |
| 2016/0046294 | A1* | 2/2016 | Lee | G06F 3/016 340/576 |
| 2016/0052391 | A1* | 2/2016 | Walsh | B60K 28/066 340/575 |
| 2016/0159217 | A1* | 6/2016 | Kim | B60W 50/08 340/575 |
| 2017/0242433 | A1* | 8/2017 | Ochiai | G01C 21/3484 |
| 2017/0276503 | A1* | 9/2017 | Oh | B60L 53/63 |
| 2017/0308948 | A1* | 10/2017 | Chikkannanavar | G06F 16/248 |
| 2018/0281612 | A1* | 10/2018 | Perry | B60L 53/63 |
| 2018/0357894 | A1* | 12/2018 | Bjersing | G08G 1/0141 |
| 2019/0108548 | A1* | 4/2019 | Gaither | G06Q 30/0261 |
| 2019/0130318 | A1* | 5/2019 | Lee | G07B 15/063 |
| 2019/0226861 | A1* | 7/2019 | Schimik | G01C 21/3469 |
| 2019/0283623 | A1* | 9/2019 | Takebayashi | B60L 53/67 |
| 2019/0295400 | A1* | 9/2019 | Yamaguchi | B60R 21/00 |
| 2020/0001893 | A1* | 1/2020 | Limbacher | B60W 30/18 |

FOREIGN PATENT DOCUMENTS

| | | | | |
|---|---|---|---|---|
| JP | 2013160563 A | * | 8/2013 | |
| JP | 2013171524 A | * | 9/2013 | |
| JP | 2014-013496 A | | 1/2014 | |
| JP | 2014-225167 A | | 12/2014 | |
| WO | WO-2014006835 A1 | * | 1/2014 | ......... G01C 21/3697 |
| WO | WO-2018165845 A1 | * | 9/2018 | ............ G01C 21/34 |

OTHER PUBLICATIONS

EPO machine translation of JP 2013-160563 (original JP document published Aug. 19, 2013) (Year: 2013).*

* cited by examiner

< USAGE DATABASE >

|  | CHARGING | WAITING | | TOTAL REMAINING CHARGING TIME [min] |
|---|---|---|---|---|
|  | REMAINING CHARGING TIME OF VEHICLE CHARGING [min] | CHARGE WAITING VEHICLE COUNT [COUNT] | REMAINING CHARGING TIME OF VEHICLE WAITING [min] |  |
| CHARGER A | 20 | 3 | 60 | 80 |
| CHARGER B | 0 | 0 | 0 | 0 |
| CHARGER C | 10 | 1 | 20 | 30 |
| CHARGER D | 10 | 3 | 50 | 60 |
| CHARGER E | 30 | 1 | 30 | 60 |

FIG.5

< FATIGUE INFORMATION DATABASE >

|  | CONTINUOUS DRIVING TIME T [min] | OPEN-EYE LEVEL K [%] | STEERING ENTROPY $H_p$ | FATIGUE LEVEL F |
|---|---|---|---|---|
| VEHICLE 1 | 90 | 50 | 0.4 | |
| VEHICLE 2 | 120 | 90 | 0.6 | |
| VEHICLE 3 | 60 | 80 | 0.5 | |
| VEHICLE 4 | 30 | 65 | 0.4 | |
| VEHICLE 5 | 10 | 85 | 0.7 | |

FIG.7

| | CURRENT CONTINUOUS DRIVING TIME T1 [min] | EXPECTED DRIVING TIME T2 TO CHARGER [min] | TOTAL CONTINUOUS DRIVING TIME T3 [min] | TOTAL REMAINING CHARGING TIME T4 [min] | EXPECTED WAIT TIME T5 [min] | CHARGE WAITING VEHICLE COUNT [COUNT] | RECOMMENDED RANK |
|---|---|---|---|---|---|---|---|
| | | | T3=T1+T2 | | T5=T4−T2 | | |
| CHARGER A | 90 | 15 | 105 | 80 | 65 | 3 | 4 |
| CHARGER B | 90 | 20 | 110 | 0 | 0 | 0 | 1 |
| CHARGER C | 90 | 25 | 115 | 30 | 0 | 1 | 2 |
| CHARGER D | 90 | 30 | 120 | 60 | 10 | 3 | 3 |
| CHARGER E | 90 | 35 | 125 | 60 | 0 | 1 | 5 |

| RECOMMENDED RANK | LOCATION | TRAVEL DISTANCE | EXPECTED TIME OF ARRIVAL | |
|---|---|---|---|---|
| FIRST PLACE | | | | SELECT |
| SECOND PLACE | | | | SELECT |
| THIRD PLACE | | | | SELECT |
| FOURTH PLACE | | | | SELECT |
| FIFTH PLACE | | | | SELECT |

FIG.12

| | CURRENT CONTINUOUS DRIVING TIME T1 [min] | EXPECTED DRIVING TIME T2 [min] | TOTAL CONTINUOUS DRIVING TIME T3 [min] T3=T1+T2 | TOTAL REMAINING CHARGING TIME T4 [min] | EXPECTED WAIT TIME T5 [min] T5=T4−T2 | NECESSARY CHARGING TIME T6 [min] | CHARGING COMPLETION TIME T7 [min] T7=T5+T6 | RECOMMENDED REST PERIOD T8 [min] | RECOMMENDED RANK |
|---|---|---|---|---|---|---|---|---|---|
| CHARGER A | 90 | 15 | 105 | 80 | 65 | 10 | 75 | 15 | 2 |
| CHARGER B | 90 | 20 | 110 | 0 | 0 | 15 | 15 | 30 | 4 |
| CHARGER C | 90 | 25 | 115 | 30 | 0 | 20 | 20 | 30 | 3 |
| CHARGER D | 90 | 30 | 120 | 60 | 10 | 30 | 40 | 30 | 1 |
| CHARGER E | 90 | 35 | 125 | 60 | 0 | 30 | 30 | 60 | 5 |

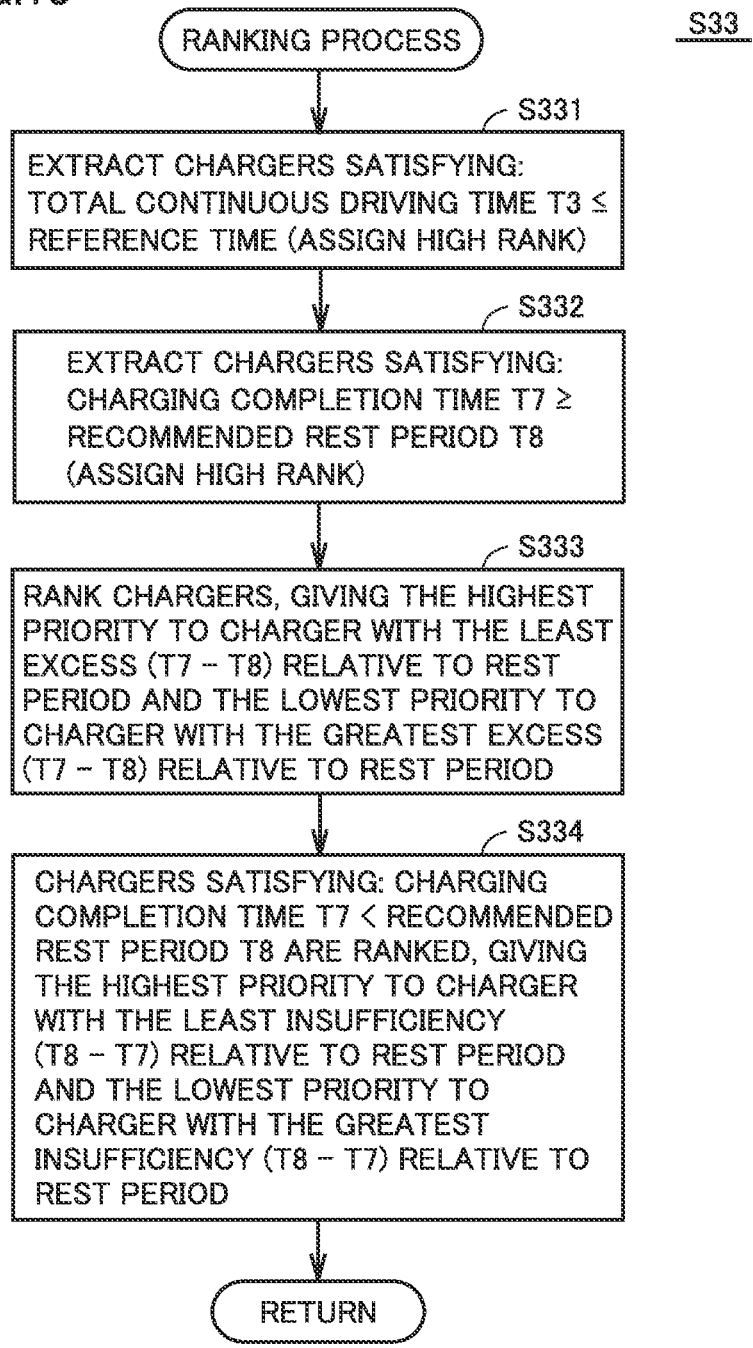

SERVER, VEHICLE, AND CHARGER INFORMATION METHOD

CROSS REFERENCE TO RELATED APPLICATIONS

This nonprovisional application claims priority to Japanese Patent Application No. 2018-178834 filed on Sep. 25, 2018 with the Japan Patent Office, the entire content of which is hereby incorporated by reference.

BACKGROUND

Field

The present disclosure relates to a server, a vehicle, a charger information method, and, more particularly, to a technology of informing a vehicle, mounted with a power storage device, of a charger.

Description of the Background Art

In recent years, vehicles (specifically, electric vehicles, plug-in hybrid vehicles, etc.) which are capable of charging an in-vehicle power storage device using externally supplied power (what is known as external charging) are increasingly popular. In general, while fueling of gasoline or the like takes time as short as a few minutes, charging a vehicle takes long (typically, tens of minutes to a few hours). Therefore, when a driver's vehicle needs charging by a charger of the go (also called a charge spot, a charging station) and that charger is in use by another vehicle, the driver's vehicle is unable to start charging until the charging by the another vehicle is completed. Accordingly, to improve the driver conveniences, it is desirable that a driver is able to ascertain, without having to go to chargers, a charger to select to start charging promptly.

For example, the information system disclosed in Japanese Patent Laying-Open No. 2014-225167 has a feature of producing information on an expected operational status of a charger at an expected time of arrival of a vehicle, from past operational statuses.

SUMMARY

The inventor had the insight that the following problem could occur. As technology development in power storage devices, such as secondary batteries, advances and the cost declines going forward, the capacities (full charge capacities) of power storage devices are expected to increase. Consequently, the remaining travel distance (what is known as EV travel distance) of the vehicle also extends, which extends the driving time without charging. On the other hand, generally, as a driver drives a vehicle for an extended period of time, the driver's fatigue is accumulated. This indicates that with an extended period of time for which the vehicle is allowed to travel without charging, the driver's fatigue can be a problem.

The present disclosure is made to solve the above problem and an object of the present disclosure is to inform a driver of a suitable charger, taking his/her fatigue into an account.

(1) A server according to a certain aspect of the present disclosure informs a vehicle of a charger, the vehicle being mounted with a power storage device. The vehicle includes a fatigue detection device configured to detect a fatigue level of a driver. The server includes: a communication device configured to receive, from the vehicle, information indicative of the fatigue level of the driver detected by the fatigue detection device; and a processor configured to, when the fatigue level of the driver is above a given reference value, extract at least one charger installed within an accessible range of the vehicle, based on power stored in the power storage device, a current location of the vehicle, and usage of the at least one charger, and inform the vehicle of the extracted charger.

According to the above configuration (1), when the fatigue level of the driver is above the given reference value, the driver is informed of chargers. This allows the driver to be informed of chargers before the driver's fatigue is accumulated too much.

(2) When a plurality of chargers are extracted, the processor is configured to rank the extracted chargers. The processor ranks the extracted chargers, giving a higher priority to a charger a continuous driving time for which is below a given reference time than a charger the continuous driving time for which is above the reference time, the continuous driving time being a time since the driver starts driving the vehicle until the vehicle arrives at the charger.

The driver is allowed to rest while the vehicle is being charged. According to the above configuration (2), since a charger for which the continuous driving time of the driver is below the reference time (120 minutes in the example described below) is assigned a higher rank, by selecting a charger having a high rank, the driver is able to take a rest before the continuous driving time exceeds the reference time.

(3) Among the extracted chargers, the processor is configured to rank chargers the continuous driving time for which is above the reference time, giving a highest priority to a charger with a shortest wait time and a lowest priority to a charger with a longest wait time, the wait time being a time since a time of arrival of the vehicle at the charger until the vehicle is allowed to start charging.

According to the above configuration (3), a charger the wait time for which is shorter is set a higher rank. For this reason, by selecting a charger assigned a higher rank, the driver is able to reduce the wait time. This allows the vehicle to start charging promptly, and an increased driver convenience is achieved.

(4) When there are a plurality of chargers the wait time for which is the same, the processor is configured to rank the plurality of chargers, giving a highest priority to a charger at which a least number of other vehicles are waiting for charging and a lowest priority to a charger at which a greatest number of other vehicles are waiting for charging.

After a vehicle has finished charging at a charger, payment of the charging fee may take time before another vehicle begins charging using that charger, the above two vehicles may not be smoothly docked out and in to the charger one after another. According to the above configuration (4), a charger for which the number of vehicles waiting is less is assigned a higher rank. This reduces the number of vehicles to be docked out and in to a charger, which allows the vehicle of the driver to start charging even more promptly, and an increased driver convenience is achieved.

(5) When a plurality of other vehicles are waiting for charging, the processor is configured to rank the plurality of chargers, giving a highest priority to a charger requiring a shortest driving time by the driver and a lowest priority to a charger requiring a longest driving time by the driver, the driving time being a time taken for the vehicle to arrive at the charger.

According to the above configuration (5), a charger the driving time by the driver for which is shorter, is assigned a higher rank. This allows the driver to shorten the driving time and take a rest earlier.

(6) When a plurality of chargers are extracted and the fatigue level of the driver is above another reference value higher than the reference value, the processor is configured to rank the plurality of chargers, giving a highest priority to a charger that is closer to the current location of the vehicle.

According to the above configuration (6), another reference value is set for a value indicating that the driver's fatigue is extremely accumulated, and when the driver's fatigue is accumulated, the driving time that takes the driver to arrive at the charger is thereby minimized so that the driver can take a rest earliest.

(7) When a plurality of chargers are extracted and a given mode (e.g., a mode for reducing the number of times the driver is notified of charger information) is selected by the driver, the processor is configured to rank the plurality of chargers, giving a highest priority to a charger that is farthest away from the current location of the vehicle.

If the driver is separately notified of charger information that is based on the fact that the power stored in the power storage device is depleting and charger information that is based on the fatigue level of the driver, some driver may feel such notifications annoying. Or, some driver, when he/she has an urgent thing to be done, may not wish an increased number of stops of vehicle 1. According to the above configuration (7), the number of times the driver is notified of charger information can be reduced and the number of times the driver takes a rest can be minimized.

(8) When a plurality of chargers are extracted, the processor is configured to rank the extracted chargers. The processor is configured to calculate a charging completion time since a time of arrival of the vehicle at a charger until the vehicle completes charging using the charger, and calculate a recommended rest period based on the fatigue level of the driver, the recommended rest period being a rest period during which the driver is recommended to rest while the vehicle is being charged using the charger; and assign a higher priority to a charger the charging completion time for which is above the recommended rest period, than a charger the charging completion time for which is below the recommended rest period.

According to the above configuration (8), a charger the charging completion time for which is longer than the recommended rest period is assigned a higher rank. For this reason, by selecting a charger assigned a higher rank, the driver is able to rest sufficiently to recover from fatigue while vehicle 1 is being charged.

(9) When there are a plurality of chargers the charging completion time for which is above the recommended rest period, the processor is configured to rank the plurality of chargers, giving a highest priority to a charger with a least excess of the charging completion time relative to the recommended rest period and a lowest priority to a charger with a greatest excess of the charging completion time relative to the recommended rest period.

If the excess of the charging completion time relative to the recommended rest period is longer than necessary, the driver, although having had a sufficient rest, still has to wait until charging of his/her vehicle is completed, which may diminish the driver convenience. According to the above configuration (9), the driver is allowed to resume driving after resting sufficiently, thereby inhibiting excessive diminishment in the driver convenience.

(10) When there are a plurality of chargers the charging completion time for which is below the recommended rest period, the processor is configured to rank the plurality of chargers, giving a highest priority to a charger with a least insufficiency in the charging completion time relative to the recommended rest period and a lowest priority to a charger with a greatest insufficiency in the charging completion time relative to the recommended rest period.

According to the above configuration (10), the driver, by selecting a charger having a higher rank, is allowed to take a rest as close to the recommended rest period as possible while it is not as long as the recommended rest period.

(11) A vehicle according to another aspect of the present disclosure is configured to charge a power storage device mounted in the vehicle, using power supplied external to the vehicle. The vehicle includes a fatigue detection device configured to detect a fatigue level of a driver of the vehicle; and a communication device configured to transmit a charger information request to a server when the fatigue level of the driver is above a given reference value. Responsive to the charger information request, the server extracts at least one charger installed within an accessible range of the vehicle based on power stored in the power storage device, a current location of the vehicle, and usage of the at least one charger, and informs the vehicle of the extracted charger. The vehicle further includes a notification device configured to notify the driver of the charger informed of by the server.

According to the above configuration (11), as with the above configuration (1), the driver can be informed of chargers before the driver's fatigue is accumulated too much.

(12) A charger information method according to still another aspect of the present disclosure is a method for informing, by a server, a vehicle of a charger, the vehicle being mounted with a power storage device, the method includes a first step, a second step, and a third step. The first step is obtaining, by the server, an accessible range of the vehicle, the accessible range being determined by power stored in the power storage device and a current location of the vehicle. The second step is detecting a fatigue level of the vehicle. The third step is, when the fatigue level of the driver is above the given reference value, extracting, by the server, at least one charger installed within the accessible range of the vehicle based on the power stored in the power storage device, the current location of the vehicle, and the usage of the at least one charger, and informing, by the server, the vehicle of the extracted charger.

According to the above method (12), as with the above configuration (1), the driver can be informed of a charger before the driver's fatigue is accumulated too much.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 5 is a conceptual diagram for illustrating information stored in a fatigue information database.

FIG. 7 is a conceptual diagram for illustrating a ranking process according to Embodiment 1.

FIG. 12 is a conceptual diagram for illustrating more details of the ranking process according to Embodiment 1.

FIG. 13 is a flowchart for illustrating more details of a ranking process according to Embodiment 2.

DETAILED DESCRIPTION

Hereinafter, the present embodiment will be described below in detail, with reference to the accompanying drawings. Note that the same reference signs are used to refer to the same or like parts, and the description thereof will not be repeated.

Embodiment 1

Configuration of Charger Information System

Figure 1:
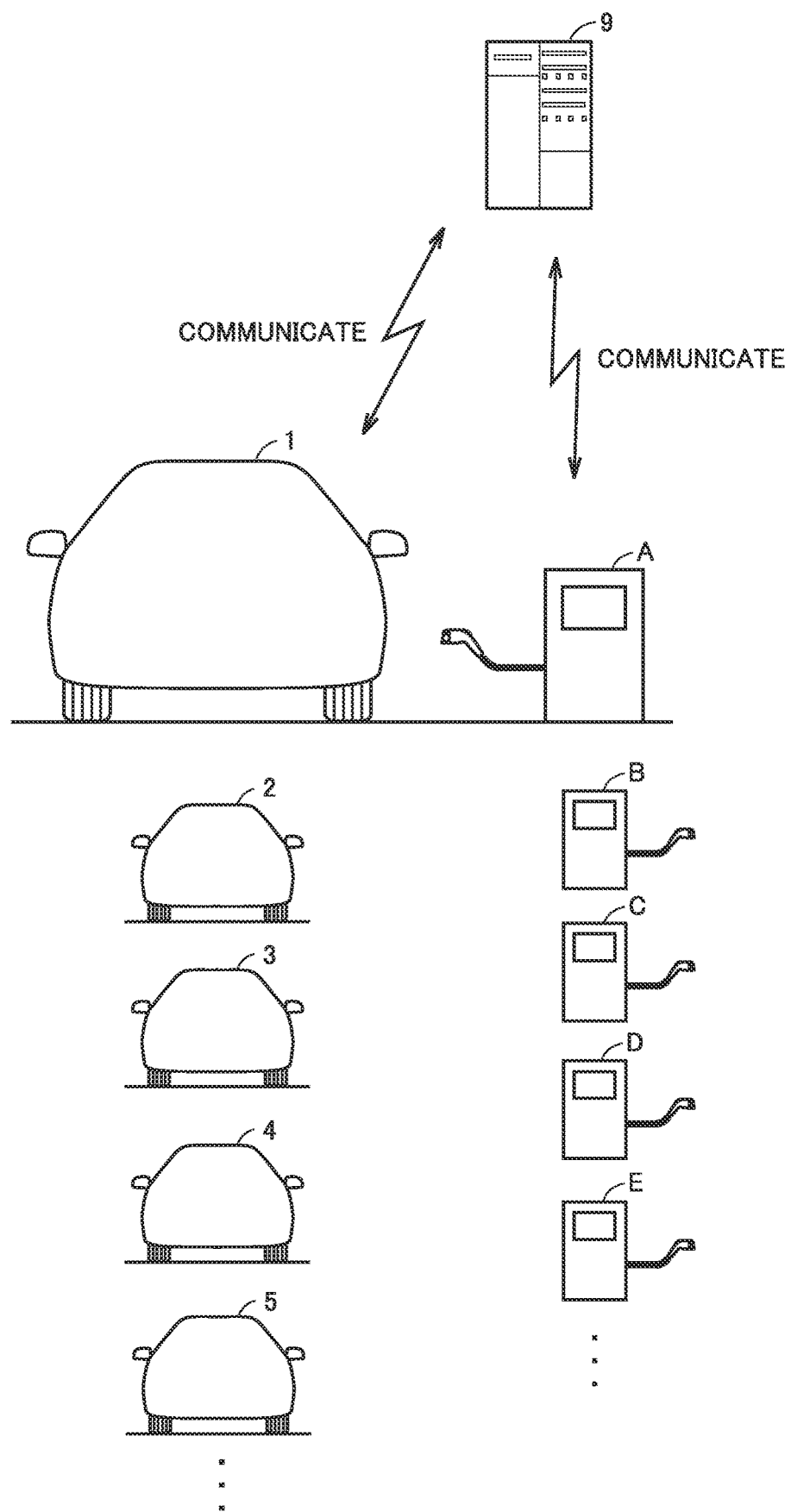
FIG. 1 is a diagram schematically showing an overall configuration of a charger information system according to Embodiment 1.

FIG. 1 is a diagram schematically showing an overall configuration of a charger information system according to Embodiment 1. Referring to FIG. 1, the charger information system includes multiple vehicles 1 to 5, and a server 9. Vehicles 1 to 5 are, for example, electric vehicles each mounted with a battery 110 (see FIG. 2). Vehicles 1 to 5 are each configured to charge (plug-in charge) battery 110 with power supplied from any of chargers (chargers A to E in FIG. 1).

Vehicle 1 and server 9 are configured to bidirectionally communicate with each other. The same is true for between the other vehicles 2 to 4 and server 9. With this, server 9 receives/transmits necessary information from/to vehicles 1 to 5. Chargers A to E and server 9 are also configured to bidirectionally communicate with each other. With this, server 9 collects information indicative of the usages of chargers A to E.

While, for the sake of brevity, the embodiment will be described with reference to a configuration of the charger information system including five vehicles 1 to 5, it should be noted that the number of vehicles included in the charger information system is not particularly limited. Moreover, more than 5 chargers may be provided.

Figure 2:
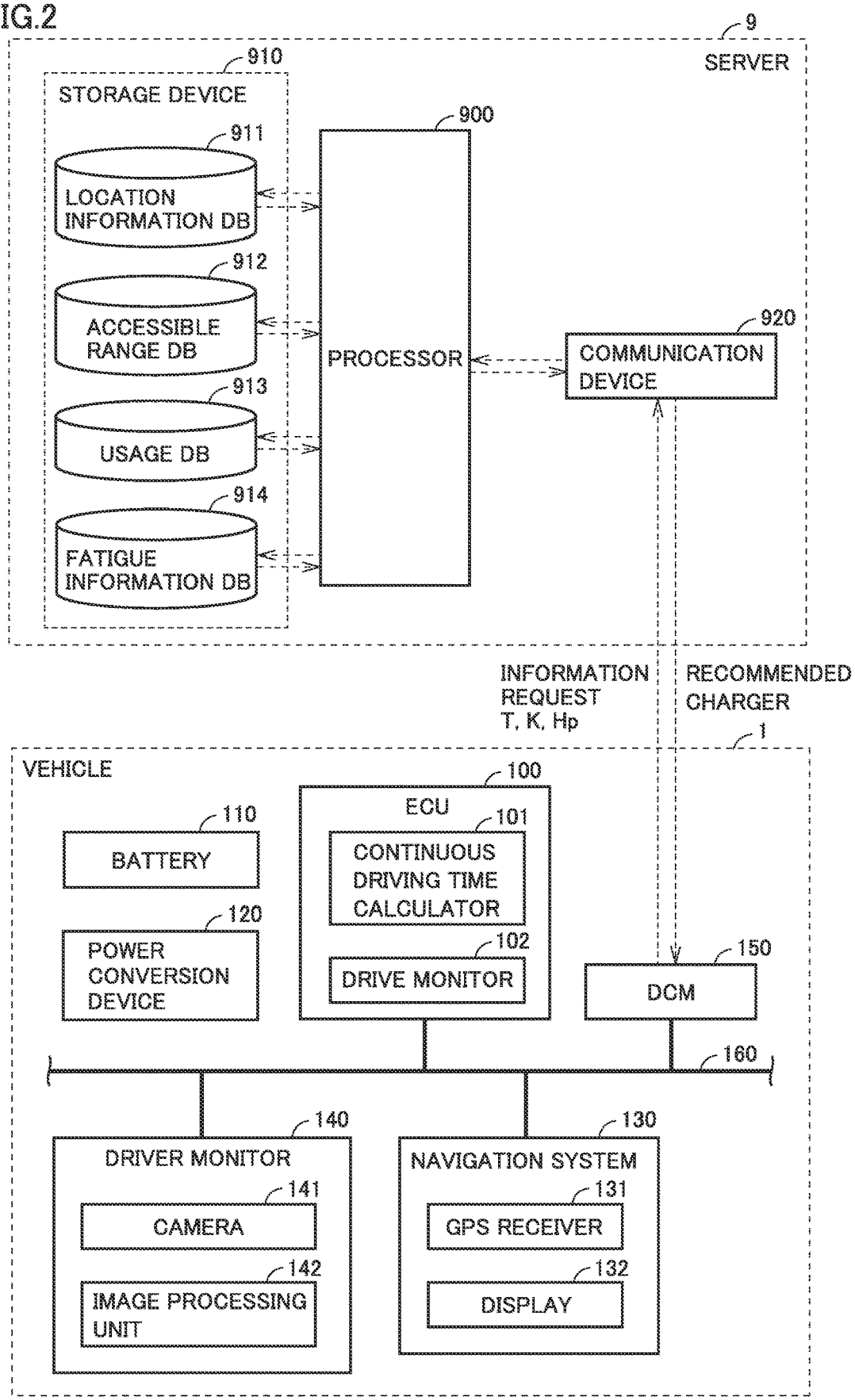
FIG. 2 is a diagram showing more details of the configuration of the charger information system.

FIG. 2 is a diagram showing more details of the configuration of the charger information system. Vehicles 2 to 5 basically have the same configuration as vehicle 1. Thus, in the following, the configuration of vehicle 1 will be representatively described.

Referring to FIG. 2, vehicle 1 includes an electronic control unit (ECU) 100, a battery 110, a power conversion device 120, a navigation system 130, a driver monitor 140, and a communication module 150. ECU 100, navigation system 130, driver monitor 140, and communication module 150 are connected to one another by a wired, vehicle network 160 such as a controller area network (CAN).

Battery 110 is a battery pack configured with multiple cells (not shown). Each cell is a secondary battery, such as a lithium-ion secondary battery or a nickel-metal hydride battery. Battery 110 supplies, via a power control unit (PCU) (not shown), a motor generator (not shown) with power for driving the motor generator. The motor generator is also able to generate power by regenerative braking. Alternating-current (AC) power generated by the motor generator is converted into direct-current (DC) power by the power control unit and the DC power is charged in battery 110. Note that a capacitor, such as an electric double layer capacitor, may be employed, instead of the secondary battery.

According to a control signal from ECU 100, power conversion device 120 converts the power supplied from chargers A to E into DC power having a voltage that is chargeable in battery 110.

Navigation system 130 includes a global positioning system (GPS) receiver 131 for identifying the location of vehicle 1, based on a radio wave from an artificial satellite (not shown), and a touch panel display 132 which displays various information and receives various driver operations. Navigation system 130 performs various navigation processes for vehicle 1, using the positional information (hereinafter, also referred to as "GPS information") of vehicle 1 identified by GPS receiver 131.

More specifically, navigation system 130 displays, on display 132, a road map around vehicle 1 based on the GPS information of vehicle 1 and road map data stored in a memory (not shown). The current location of vehicle 1 and locations of one or more chargers are overlapped on the road map. Navigation system 130 also receives a driver operation of selecting any one of the one or more chargers displayed on display 132. Navigation system 130 then shows a recommended route from the current location of vehicle 1 to the charger (a destination or a stop) selected by the driver. Note that navigation system 130 (more specifically, touch panel display 132) corresponds to a "notification device" according to the present disclosure.

Driver monitor 140 is configured to monitor the biometric information of the driver to detect a fatigue level of the driver. Driver monitor 140 includes, for example, a camera 141 and an image processing unit 142.

Camera 141 is arranged near the driver's seat (e.g., near the rear view mirror) to capture an image of the driver. Camera 141 may be provided with a light source (not shown), such as a light emitting diode (LED) which emits near-infrared light to the driver's face so that an image of the driver's face can be captured even at night.

Image processing unit 142 is configured to perform a face image recognition process. Image processing unit 142 extracts the driver's face from the image captured by camera 141, and calculates, for example, an "open-eye level" K indicative of an open/closed state of the driver's eyes from the extracted face image. Open-eye level K indicates the percentage of an amount of time in which the eyes are open (=an amount of time in which the pupils are captured/total time). The less the open-eye level K is, the lower the degree of the driver's alertness is, that is, the higher the driver's fatigue level F (including drowsiness) is.

Note that driver monitor 140 is not limited to one that is configured to calculate the driver's open-eye level K, and may monitor other biometric information of the driver, alternatively or in addition to the driver's open-eye level K. For example, driver monitor 140 is capable of monitoring at least one of the driver's body movements, the orientation of the driver's face, and the driver's facial expressions.

Communication module 150 is an in-vehicle data communication module (DCM), and configured to allow ECU 100 to perform bidirectional communications with server 9.

ECU 100 is configured with a central processing unit (CPU), a memory, and I/O ports (none of which are shown). ECU 100 controls each device in vehicle 1 based on various sensors (not shown) measurements and programs stored in the memory so that vehicle 1 is brought into a desired state. ECU 100 also generates various information to transmit to server 9. Specifically, ECU 100 includes a continuous driving time calculator 101 and a drive monitor 102.

Continuous driving time calculator 101 is configured with a timer (not shown) and calculates a continuous driving time of vehicle 1. More specifically, continuous driving time calculator 101 can calculate, as a continuous driving time of vehicle 1, an elapsed time since the transmission (not shown) of vehicle 1 has been changed from a non-traveling position, such as the park (P) position, to the drive (D) position until the current time. Alternatively, the continuous driving time of vehicle 1 may be an elapsed time since an ignition on (IG-ON) time of vehicle 1 until the current time. Moreover, the continuous driving time of vehicle 1 can be reset a predetermined period (e.g., about 5 minutes) after the transmission of vehicle 1 is returned to the park (P) position and the ignition off (IG-OFF) operation of vehicle 1 is performed.

However, in some embodiments, the continuous driving time of vehicle 1 may not be calculated within ECU 100. The continuous driving time of vehicle 1 may be calculated by driver monitor 140 monitoring the driver's biometric information (information on the driver's body movements, the orientation of the face, and facial expressions). The continuous driving time of vehicle 1 can also be calculated by navigation system 130 monitoring the travel conditions of vehicle 1.

Drive monitor 102 is configured to monitor the situation of driving vehicle 1 by a "steering entropy method," which quantifies the smoothness of the driver's steering using, for example, the steering wheel angle. Since the steering entropy method is well known, the detailed description thereof will not be repeated here. The less the steering entropy value Hp is, more smoothly the driving operation by the driver is carried out, indicating that the driving of vehicle 1 is stable. In contrast, the greater the steering entropy value Hp is, less smoothly the driving operation by the driver is carried out, indicating that the driving of vehicle 1 is unstable.

Note that navigation system 130, driver monitor 140, and ECU 100 (continuous driving time calculator 101) correspond to a "fatigue detection device" according to the present disclosure. However, the "fatigue detection device" according to the present disclosure may be one or two of navigation system 130, driver monitor 140, and ECU 100.

Server 9 includes a processor (processing unit) 900, which is, for example, an application server, a storage device 910, and a communication device 920. Storage device 910 includes a location information database 911, an accessible range database 912, a usage database 913, and a fatigue information database 914.

Location information database 911 stores the GPS information of vehicles 1 to 5. The GPS information of vehicles 1 to 5 are periodically sent from vehicles 1 to 5 to server 9. Location information database 911 also stores location information of chargers A to E. A new charger may be installed or an existing charger may be removed from service. Thus, the location information of chargers stored in location information database 911 are periodically kept up-to-date by an administrator of location information database 911. Note that location information database 911 may be composed of two databases, that is, a database storing the GPS information of vehicles 1 to 5, and a database storing the location information of chargers A to E.

Accessible range database 912 stores information (access range information) about accessible ranges for vehicles 1 to 5, based on the current locations, remaining travel distances, and destinations (stops) of vehicles 1 to 5.

Communication device 920 is configured to perform bidirectional data communications with communication module 150 mounted on vehicle 1. Although not shown, communication device 920 is configured to perform bidirectional data communications also with the respective communication modules included in chargers A to E.

Processor 900 collects information (see FIG. 3) about the usages of chargers A to E via communication device 920, and causes usage database 913 to store the collected information. Processor 900 also collects information (see FIG. 5) indicative of fatigue levels of the drivers of vehicles 1 to 5 via communication device 920, and calculates fatigue level F of each driver from the collected information. Processor 900 then causes fatigue information database 914 to store the information on the calculated fatigue level F. These information will be described in detail, with reference to FIGS. 4 and 5.

Charger Information Process

Primarily processes performed by processor 900 configured as the above include a process of informing each of vehicles 1 to 5 of a charger desired to charge with. Here, the process will be described in detail, with reference to a situation in which vehicle 1 is traveling. Note that, in the following, processes performed by processor 900 will be described as processes by "server 9," for clarity of description.

Figures 3, 4:
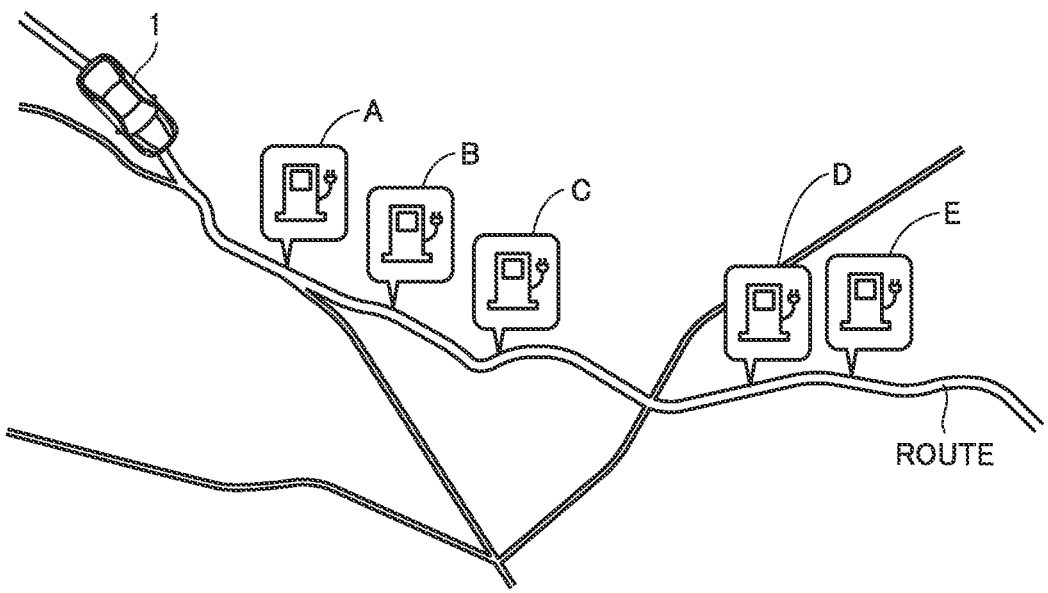
FIG. 3 is a diagram illustrating an example situation where the charger information system is used.
FIG. 4 is a conceptual diagram for illustrating information stored in a charge spot usage database.

FIG. 3 is a diagram illustrating an example situation where the charger information system is used. Referring to FIG. 3, it is assumed that vehicle 1 is traveling from the left to the right in the figure, along a proposed travel route (indicated by ROUTE) recommended by navigation system 130. Chargers A to E are installed at five locations along the proposed travel route within the accessible range for vehicle 1.

Responsive to a charger information request from vehicle 1, server 9 refers to usage database 913 to read information indicative of the usages of chargers A to E, and refers to fatigue information database 914 to read information indicative of fatigue level F of the driver of vehicle 1. Server 9 then informs vehicle 1 of an appropriate charger, based on these information.

Charger Usage

FIG. 4 is a conceptual diagram for illustrating the information stored in charger usage database 913. In the example shown in FIG. 4, a vehicle is being charged at charger A, and the remaining charging time is 20 minutes. Moreover, three vehicles are waiting for charging (or reserve charging) at charger A, and the charging time for these three vehicles is expected to be 60 minutes in total. In this case, the total of the remaining charging time (total remaining charging time) at charger A is 20 minutes+60 minutes=80 minutes. Similarly to charger A, the total remaining charging time is also calculated for each of the remaining chargers B to E.

Driver's Fatigue Level

FIG. 5 is a conceptual diagram for illustrating the fatigue information stored in fatigue information database 914. Referring to FIG. 5, in the present embodiment, the driver's fatigue level F is calculated based on a continuous driving time T (equal to T1 described below) of the vehicle, the driver's open-eye level K, and steering entropy value Hp. More specifically, fatigue level F is calculated by adding the continuous driving time T, open-eye level K, and steering entropy value Hp in certain proportions, as shown in the following Equation (1).

$$F=\alpha T+\beta K+\gamma Hp \quad (1)$$

In the example shown in FIG. 5, fatigue level F of the driver of vehicle 1 is calculated to be 120T+10K+0.5Hp. The same holds true for fatigue levels F of the drivers of the other vehicles 2 to 5.

Coefficient $\alpha$ for continuous driving time T, coefficient $\beta$ for open-eye level K, and coefficient $\gamma$ for steering entropy value Hp in Equation (1) are determined by an optimization algorithm so that they best fit the data (a large number of combinations of continuous driving time T, open-eye level K, and steering entropy value Hp, what is known as big data) which are actually acquired from a large number of vehicles. Coefficients $\alpha$, $\beta$, $\gamma$ can be determined by a machine learning using a gradient method, for example, as described below.

Continuous driving time T, open-eye level K, and steering entropy value Hp are acquired from a certain vehicle (described as "vehicle V") while vehicle V is traveling. In a predetermined period (e.g., a few to tens of minutes) since the acquisition time, if a vehicle status indicating that the fatigue of the driver of vehicle V has been accumulated is detected, e.g., if hard braking, swerving, weaving (vehicle V getting out of the lane with no blinker), or collision, etc. of vehicle V is detected, fatigue level F=100. On the other hand, if no such a vehicle status is detected, fatigue level F=0. Accordingly, the combination of the three values (T, K, Hp) are substituted into Equation (1), yielding an equation having three coefficients $\alpha$, $\beta$, $\gamma$ as unknowns.

In vehicle V, for example, an equation having coefficients $\alpha$, $\beta$, $\gamma$ as unknowns can be continuously acquired by repeating the above series of process steps for every given period. The same processing is executed with respect to the vehicles other than vehicle V. As a result, a large number of equations are acquired from a large number of vehicles.

Combinations of three coefficients $\alpha$, $\beta$, $\gamma$ are calculated by a gradient method ($\alpha$, $\beta$, $\gamma$) so as to best fit the large number of equations acquired as such. More specifically, a combination ($\alpha$, $\beta$, $\gamma$) is calculated by the machine learning so that the mean-squared error $J=(\alpha T+\beta K+\gamma Hp-F)^2$ for Equation (1) is minimum. Use of the calculated coefficients $\alpha$, $\beta$, $\gamma$ allows fatigue level F to be calculated from continuous driving time T, open-eye level K, and steering entropy value Hp. Note that at least one parameter, among continuous driving time T, open-eye level K, steering entropy value Hp, and fatigue level F, corresponds to the "driver's fatigue level" according to the present disclosure.

Charger Information Process Flow

In the charger information system, when the driver's fatigue is determined to be accumulated, the driver is informed of chargers. The following flowchart is described, with reference to a configuration in which server 9 informs the driver of vehicle 1 of chargers, taking into an account the situation shown in FIG. 3.

Figure 6:
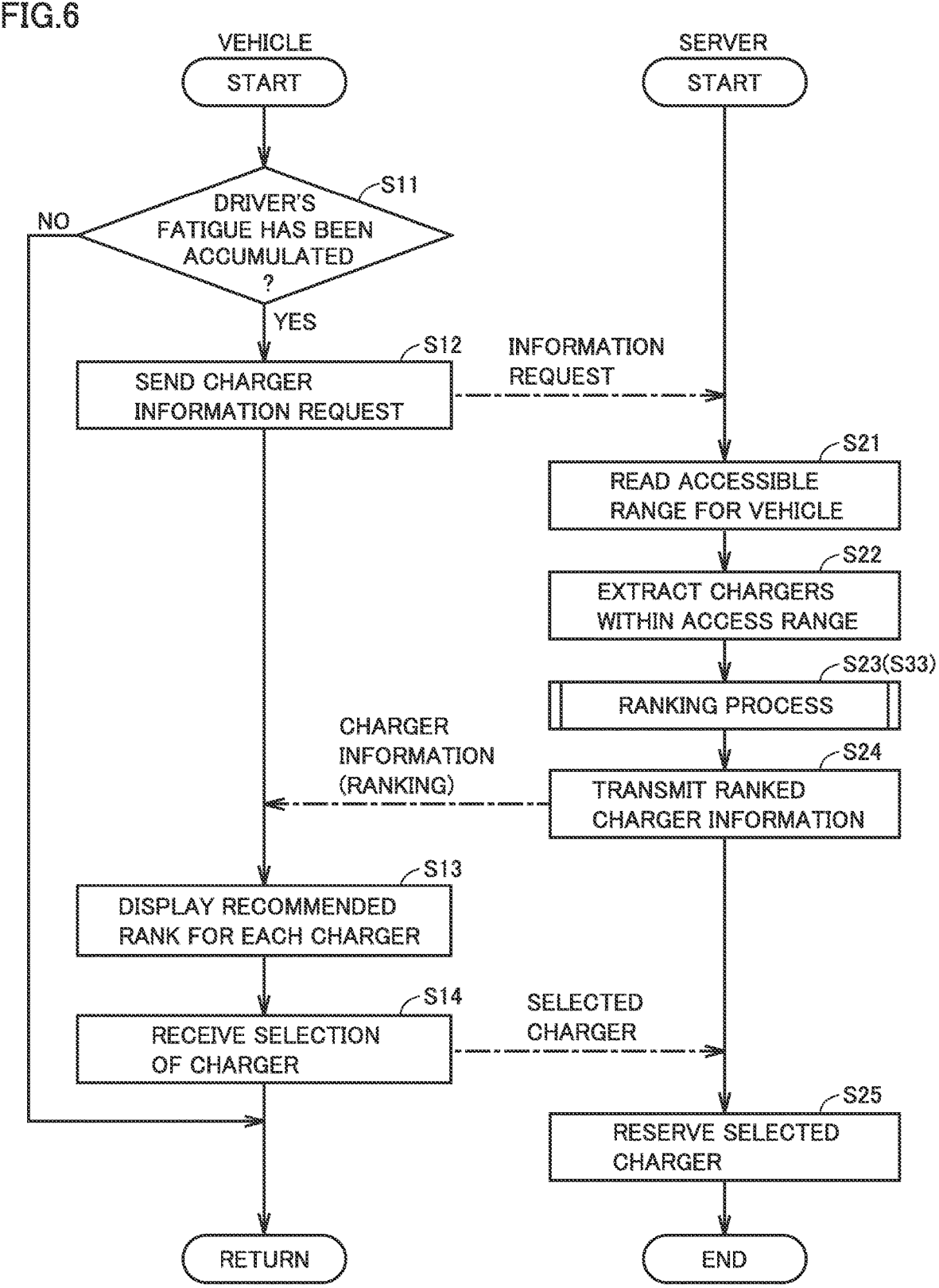
FIG. 6 is a flowchart showing a series of process steps of informing of a charger, according to Embodiment 1.

FIG. 6 is a flowchart showing a series of process steps of informing the driver of a charger, according to Embodiment 1. The flowchart shows process steps performed by vehicle 1 (ECU 100) on the left side of the figure, and process steps performed by server 9 (processor 900) on the right side of the figure. These process steps are repeated every time a given condition is satisfied or at given intervals.

Note that each process step (hereinafter, abbreviated as "S") included in FIG. 6 and each flowchart described below is basically implemented by software processing by ECU 100 or server 9 (processor 900), but may be implemented by dedicated hardware (electric circuits) fabricated within ECU 100 or server 9.

Although not shown, ECU 100 periodically calculates continuous driving time T of vehicle 1, open-eye level K of the driver of vehicle 1, and steering entropy value Hp, and transmits results of the calculations to server 9. Server 9 calculates fatigue level F of the driver of vehicle 1 from the results of the calculations, and periodically keeps fatigue information database 914 up-to-date. Since the methods of calculation of these parameters have been described in detail with reference to FIGS. 2 and 5, the descriptions thereof will not be repeated now.

At S11, based on the above parameters, ECU 100 determines whether the fatigue of the driver of vehicle 1 has been accumulated. Specifically, fatigue of the driver of vehicle 1 is determined to be accumulated if fatigue level F of the driver is above a given reference value. A determination value may be provided for each of continuous driving time T, open-eye level K, and steering entropy value Hp. Continuous driving time T, open-eye level K, and steering entropy value Hp are each compared with a corresponding determination value, and the driver's fatigue is determined to be accumulated if at least one of continuous driving time T, open-eye level K, and steering entropy value Hp is above a corresponding determination value.

Note that whether the fatigue of the driver of vehicle 1 has been accumulated or not may be determined by server 9, instead of vehicle 1. Server 9 can make the determination, if the driver's fatigue level F is periodically transmitted from vehicle 1 to server 9.

If the fatigue of the driver of vehicle 1 is determined to be accumulated (YES at S11), ECU 100 sends to server 9 a request to inform vehicle 1 of an appropriate charger (S12).

Upon receipt of the charger information request from vehicle 1, server 9 refers to accessible range database 912 to read an accessible range for vehicle 1 (S21). While FIG. 3 has been described with reference to the example in which the proposed travel route (ROUTE) for vehicle 1 is determined, it should be noted that there is also a case where the destination of vehicle 1 is undetermined, and a proposed travel route for vehicle 1 is unknown to server 9. In this case, the accessible range of vehicle 1 can be set to, for example, a circular region having the current location of vehicle 1 as the center and the remaining travel distance of vehicle 1 as the radius.

At S22, server 9 refers to the charger location information stored in location information database 911 to extract chargers that are installed within the access range of vehicle 1 read at S21. In the example shown in FIG. 3, chargers A to E at five locations within the access range of vehicle 1 are extracted.

At S23, among the chargers extracted at S22, server 9 determines a recommendation ranking of the chargers to inform vehicle 1 of (the ranking process).

FIG. 7 is a conceptual diagram for illustrating the ranking process (process step S23) according to Embodiment 1. In Embodiment 1, server 9 ranks the chargers for recommendation to the driver of vehicle 1, using six index values shown in FIG. 7.

A first index value is the current continuous driving time T1 of vehicle 1. A second index value is a time (expected driving time) T2 expected to take the driver to drive vehicle 1 from the current location to charger A to E. A third index value is an expected total continuous driving time T3 of vehicle 1 to charger A to E. Total continuous driving time T3 is calculated as the sum (T1+T2=T3) of continuous driving time T1 and expected driving time T2.

A fourth index value is a current total remaining charging time T4 of charger A to E. Total remaining charging time T4 is calculated as the sum of the remaining charging time of a vehicle that is currently charging and the remaining charging time of a vehicle that is waiting, as described with reference to FIG. 4.

A fifth index value is a wait time (expected wait time) T5 since the time of arrival of vehicle 1 at charger A to E until vehicle 1 starts charging. Expected wait time T5 for a charger is calculated by subtracting expected driving time T2 for that charger from total remaining charging time T4 of the charger (T5=T4−T2). Note that, if expected wait time T5 as a result of this calculation yields a negative value, expected wait time T5 is set to zero.

A sixth index value is the number of vehicles waiting for charging at charger A to E (charge waiting vehicle count), which is the same number of vehicles described with reference to FIG. 4.

Figure 8:
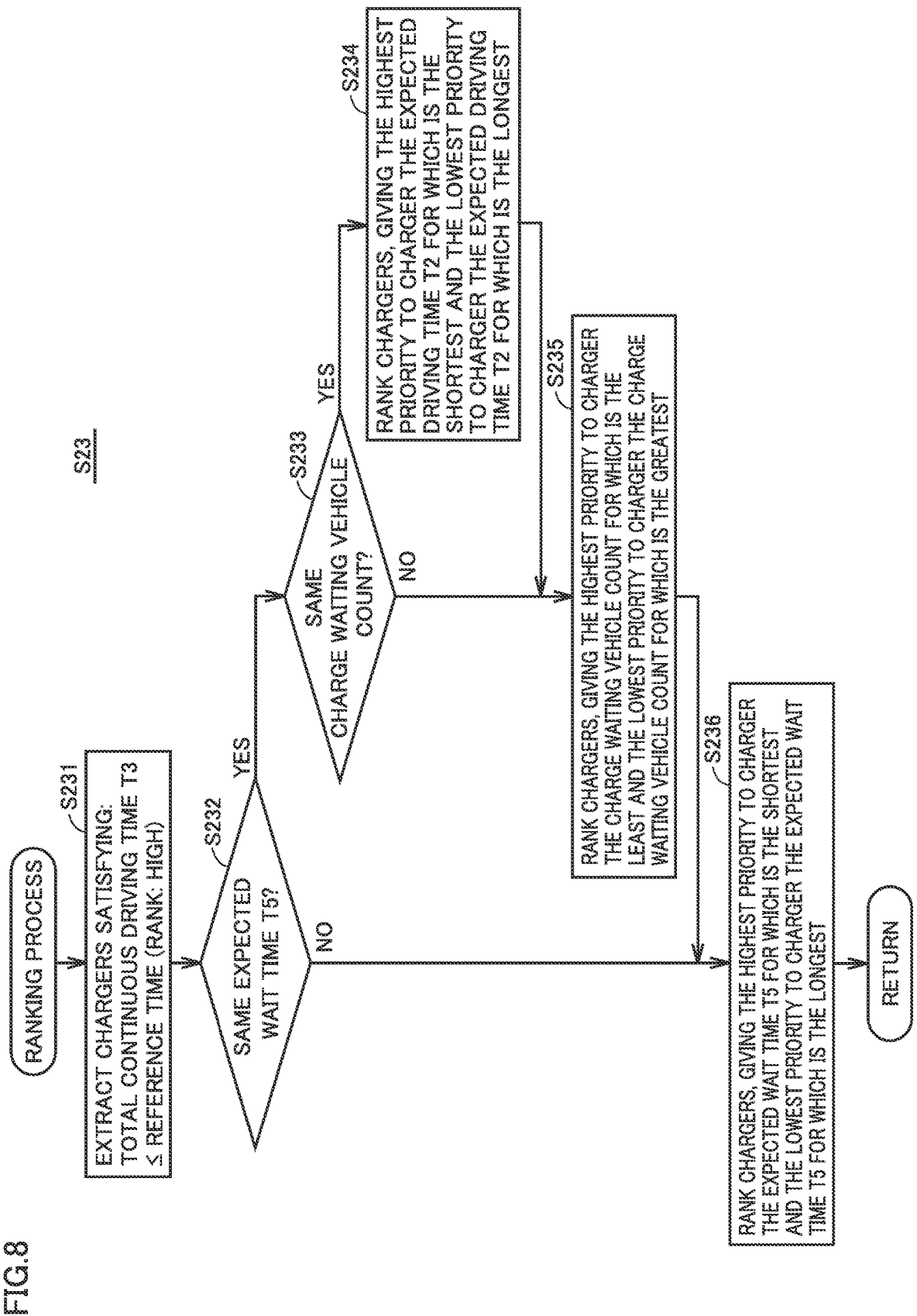
FIG. 8 is a flowchart for illustrating more details of the ranking process according to Embodiment 1.

FIG. 8 is a flowchart for illustrating more details of the ranking process according to Embodiment 1. Referring to FIGS. 7 and 8, at S231, server 9 extracts chargers the total continuous driving time T3 for which is less than or equal to a given reference time, from among chargers A to E that are installed within the access range of vehicle 1. Server 9 then ranks the chargers, giving a higher priority to a charger the total continuous driving time T3 for which is less than or equal to the given reference time than a charger the total continuous driving time T3 for which is longer than the reference time. Here, the reference time is a duration after which the driver is desired to stop driving and take a rest, which is about a few hours.

In Embodiment 1, as one example, the reference time is set to 120 minutes. Consequently, chargers A to D are extracted from among chargers A to E, and chargers A to D are assigned higher ranks than the rest of others, as shown in FIG. 7. On the other hand, charger E the total continuous driving time T3 for which is above the reference time, 120 minutes, is not recommended to the driver of vehicle 1. Thus, vehicle 1 is informed of charger E with the lowest rank. However, vehicle 1 may not be informed of any charger (charger E) that has failed to meet the above criteria and is not extracted by server 9.

At S232, server 9 determines whether there are chargers the expected wait times T5 for which are the same, among the chargers extracted at S231.

In the example shown in FIG. 7, expected wait time T5 of charger B and expected wait time T5 of charger C are the same, both zero minute (YES at S232). Consequently, server 9 passes the process to S233 and further determines whether there are chargers the charge waiting vehicle counts for which are the same, among those that have the same expected wait time T5.

When there are chargers the charge waiting vehicle counts for which are the same (YES at S233), server 9 ranks the chargers having the same expected wait time T5, giving the highest priority to a charger the expected driving time T2 for which is the shortest and the lowest priority to a charger the expected driving time T2 for which is the longest (S234). Server 9 then passes the process to S235. On the other hand, when there are no chargers the charge waiting vehicle counts for which are the same at S233 (NO at S233), server 9 skips process step S234 and passes the process to S235. At S235, server 9 ranks the chargers having the same expected wait time T5, giving the highest priority to a charger the charge waiting vehicle count for which is the least and the lowest priority to a charger the charge waiting vehicle count for which is the greatest.

In the example shown in FIG. 7, the charge waiting vehicle count for charger B is zero, and the charge waiting vehicle count for charger C is one. In other words, the charge waiting vehicle counts for chargers B and C are not the same. Accordingly, the process is passed to S235 without through S234, and charger B the charge waiting vehicle count for which is less than charger C is assigned a higher rank than charger C.

After the execution of process step S235, the process is passed to S236. At S236, server 9 ranks the chargers, giving the highest priority to a charger the expected wait time T5 for which is the shortest and the lowest priority to a charger the expected wait time T5 for which is the longest.

In the example shown in FIG. 7, expected wait time T5 for charger B and expected wait time T5 for charger C are both zero minute and the shortest among chargers A to E. Here, at process step S235, charger B is assigned a higher rank than charger C based on the fact that the charge waiting vehicle count for charger B is less than charger C. Consequently, charger B is placed first in the ranking and charger C is placed second in the ranking. Further, charger D the expected wait time T5 for which is the second shortest is placed third in the ranking, and charger A the expected wait time T5 for which is the longest is placed fourth in the ranking. The process is then returned to the flowchart shown in FIG. 6, and process step S24 is executed.

Referring again to FIG. 6, at S24, server 9 transmits the information on the chargers that have been assigned the ranks by the ranking process. Upon receipt of the charger information from server 9, vehicle 1 displays the charger information on display 132 of navigation system 130 (S13).

Figures 9, 10:
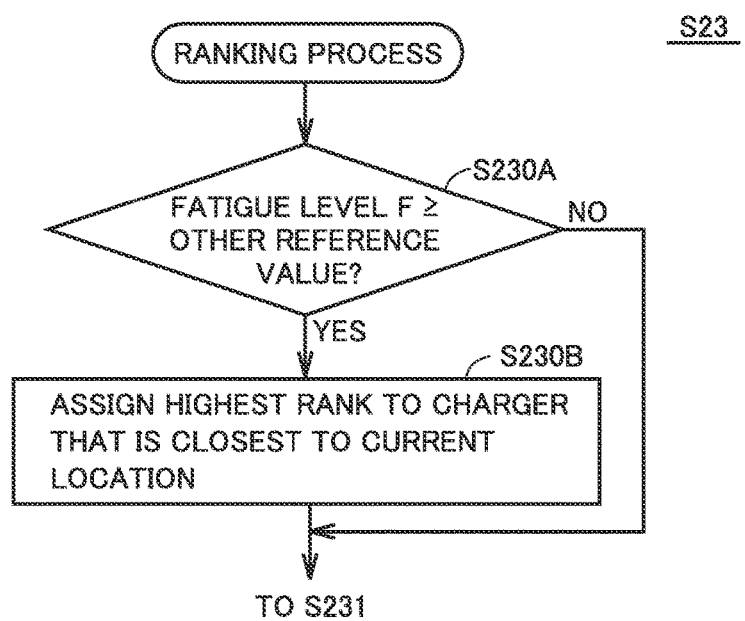
FIG. 9 is a diagram illustrating an example method of display of charger information on a display in a navigation system.
FIG. 10 is a flowchart for illustrating a ranking process according to Variation 1 of Embodiment 1.

FIG. 9 is a diagram illustrating an example method of display of the charger information on display 132 of navigation system 130. On display 132, the chargers are displayed in order from the highest recommendation rank to the lowest, along with the location where the charger is installed (e.g., a rest area or parking space name), the travel distance of vehicle 1 to the charger, and the expected time of arrival of vehicle 1 at the charger, as shown in FIG. 9. Checking such display, the driver is allowed to select a desired charger to charge with, by, for example, touching "SELECT" button on the touch panel on display 132.

Note that, if a map is shown on display 132 and the map includes icons indicative of the locations of the chargers as shown in FIG. 3, the recommendation rank for each charger icon may be displayed, in addition to (or alternative to) the display as shown in FIG. 9. As one example, the recommendation ranks can be classified by color for each icon. For example, the icon of the charger placed first in the recommendation ranking can be displayed in blue, the icon of the charger placed second in the recommendation ranking can be displayed in green, the icon of the charger placed third in the recommendation ranking can be displayed in yellow, the icon of the charger placed fourth in the recommendation ranking can be displayed in orange, and the icon of the charger placed fifth in the recommendation ranking can be displayed in red. Visualizing the recommendation ranking by color of the charger icons as such allows the driver to more readily select a charger assigned a higher recommendation rank.

Returning to FIG. 6, as vehicle 1 receives an operation of the driver selecting a charger which the driver desires to charge the vehicle with (S14), a signal indicating so is transmitted to server 9. Responsive to this signal, server 9 reserves the charger selected by the driver (S25).

As described above, in Embodiment 1, the driver can be informed of an appropriate charger, taking into an account the driver's fatigue level F (and continuous driving time T, open-eye level K, and steering entropy value Hp). More specifically, when the driver's fatigue level F is greater than or equal to the given reference value (YES at S11 of FIG. 6), a charger information request is transmitted from vehicle 1 to server 9 and the driver is informed of chargers. This allows informing the driver of chargers before the driver's fatigue is accumulated too much.

Moreover, since chargers the driver's total continuous driving time T3 for which is less than or equal to the reference time (120 minutes) are extracted at process step S231 of FIG. 8, the driver is able to take a rest before total continuous driving time T3 exceeds the reference time.

Furthermore, at process step S236, the chargers the total continuous driving time T3 for which is less than the reference time are ranked, giving a highest priority to a charger the expected wait time T5 for which is the shortest and a lowest priority to a charger the expected wait time T5 for which is the longest. This allows the driver to charge vehicle 1 promptly once vehicle 1 arrives at the charger, thereby increasing the driver convenience.

For example, payment of the charging fee may take time, and vehicles may not be smoothly docked out and in to the charger one after another (a vehicle having completed charging moves out of the charging space and another vehicle moves in to the space for charging). This problem is more prominent with a greater charge waiting vehicle count and a greater number of vehicles to be docked. In contrast, in the present embodiment, if multiple chargers do not have the same charge waiting vehicle count (NO at S233), a charger having the least charge waiting vehicle count is assigned the highest rank (S235). Consequently, the number of vehicles waiting to be docked to the charger is reduced, which causes the above problem to occur less when vehicles are docked out and in one after another. As a result, vehicle 1 is allowed to start charging even more promptly, achieving an increased driver convenience.

Furthermore, in the present embodiment, when there are multiple chargers that have the same charge waiting vehicle count (YES at S233), the chargers are ranked, giving the highest priority to a charger for which the expected driving time T2 of the driver is the shortest and the lowest priority to a charger for which the expected driving time T2 of the driver is the longest (S234). This allows the driver to take a rest earlier.

Variation 1 of Embodiment 1

If fatigue level F of the driver of vehicle 1 is higher than another reference value (a value indicating that the driver's fatigue is extremely accumulated) that is higher than the reference value used at process step S11, it is desirable to encourage the driver to take a rest immediately.

FIG. 10 is a flowchart for illustrating details of a ranking process according to Variation 1 of Embodiment 1. Referring to FIG. 10, the flowchart is different from the flowchart according to Embodiment 1 (see FIG. 8) in that the flowchart according to Variation 1 of Embodiment 1 further includes process steps S230A and S230B.

At S230A, server 9 determines whether fatigue level F of the driver of vehicle 1 is greater than or equal to the other reference value. When fatigue level F of the driver of vehicle 1 is greater than or equal to the other reference value (YES at S230A), server 9 assigns the highest rank to the charger that is located closest to the current location of vehicle 1, among the chargers installed within the access range of vehicle 1 (S230B). The process is then passed to S231. Note that when fatigue level F of the driver of vehicle 1 is less than the other reference value (NO at S230A), process step S230B is skipped and the same processing as that of Embodiment 1 is executed.

In the example shown in FIG. 3, as a result of process step S230B, charger A is placed first in the ranking. The driver selecting charger A minimizes the driving time of vehicle 1 taken until the arrival at any of the chargers. In other words, the driver of vehicle 1 is allowed to rest most promptly, which allows the driver to recover from fatigue.

Variation 2 of Embodiment 1

If the driver is separately notified of charger information that is based on the fact that the power stored in battery 110 of the vehicle is depleting and charger information that is based on the driver's fatigue level F, some driver may feel such notifications annoying. Or, some driver, when he/she has an urgent thing to be done, may not wish an increased number of stops of vehicle 1 for the driver to take a rest or to charge vehicle 1. Variation 2 will be described with reference to a configuration in which the number of notifications given to the driver is reduced and the number of times the driver takes a rest is minimized.

Figure 11:
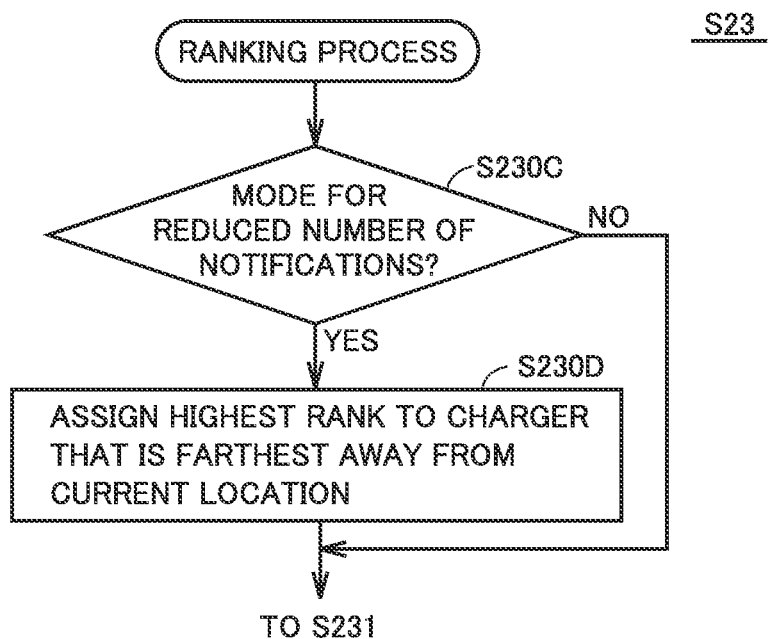
FIG. 11 is a flowchart for illustrating details of a ranking process according to Variation 2 of Embodiment 1.

FIG. 11 is a flowchart for illustrating details of a ranking process according to Variation 2 of Embodiment 1. Referring to FIG. 11, the flowchart is different from the flowchart according to Embodiment 1 (see FIG. 8) in that the flowchart according to Variation 2 of Embodiment 1 further includes process steps S230C and S230D.

At S230C, server 9 determines whether the driver has pre-selected a mode for minimizing the number of notifications to be given to the driver in vehicle 1. If the above mode is selected (YES at S230C), server 9 assigns the highest rank to a charger, among the chargers installed within the access range of vehicle 1, which is the farthest away from the current location of vehicle 1 (S230D). The process is then passed to S231. Note that when the above mode is not selected (NO at S230C), process step S230D is skipped and the same processing as that of Embodiment 1 is executed.

In the example shown in FIG. 3, charger E which is the farthest away from the current location of vehicle 1 is placed first in the ranking. If the driver of vehicle 1 selects charger E, vehicle 1 is charged with charger E, during which the driver can take a rest at charger E. In this case, the number of times the vehicle 1 stops (the number of times of charging and the number of the driver's rests) until vehicle 1 arrives at the destination is minimized. As such, the reduction of the number of stops of vehicle 1 may be prioritized, depending on the situation the driver is put in, while, as Variation 2, the driver's fatigue being accumulating may trigger a notification to the driver (see process step S11 of FIG. 6).

Embodiment 2

Embodiment 1 (and Variations 1, 2) has been described with reference to the configuration of ranking the chargers, giving the highest priority to a charger for which the expected wait time T5 upon arrival of vehicle 1 at the charger is the shortest and the lowest priority to a charger for which the expected wait time T5 upon arrival of vehicle 1 at the charger is the longest (see S236 of FIG. 8). This is because the shorter the expected wait time T5 is, the more promptly the vehicle 1 can start charging, which is highly convenient to the driver of vehicle 1. However, if vehicle 1 starts charging promptly and the charging ends so fast that the driver may end up getting back on the road, without resting sufficiently. Embodiment 2 will be described with reference to a configuration of prioritizing letting the driver take a rest sufficiently over the driver's convenience.

Note that an overall configuration of a charger information system according to Embodiment 2 is the same as the overall configuration (see FIGS. 1 and 2) of the charger information system according to Embodiment 1. The flow of the overall process of informing the driver of chargers is also the same as the flow (see FIG. 6) described with reference to Embodiment 1. The descriptions thereof will thus not be repeated.

FIG. 12 is a conceptual diagram for illustrating a ranking process according to Embodiment 2. Referring to FIG. 12, in Embodiment 2, the five index values (a first index value through a fifth index value) which are common to Embodiment 1 (see FIG. 7) are used.

The first index value is the current continuous driving time T1 of vehicle 1. The second index value is an expected driving time T2 of vehicle 1 from the current location to charger A to E. The third index value is an expected total continuous driving time T3 of vehicle 1 to charger A to E (T1+T2=T3). The fourth index value is the current total remaining charging time T4 of charger A to E. The fifth index value is a wait time (expected wait time) T5 since the time of arrival of vehicle 1 at charger A to E until vehicle 1 starts charging (T5=T4−T2).

Furthermore, in Embodiment 2, three index values (a sixth to eighth index values) described below will be used, in addition to the above five index values.

The sixth index value is a time (a necessary charging time) T6 taken to charge vehicle 1 after the arrival of vehicle 1 at charger A to E. The further the charger is away from the current location of vehicle 1, the greater the amount of power consumed by vehicle 1 until vehicle 1 arrives at the charger from the current location, which also extends the necessary charging time T6 for vehicle 1 to recover from the power consumption.

The seventh index value is a time T7 taken since the arrival of vehicle 1 at charger A to E until the completion of charging of vehicle 1 (charging completion time). Charging completion time T7 is calculated by adding necessary charging time T6 to expected wait time T5, which is from a time of arrival of vehicle 1 at charger A to E until vehicle 1 starts charging the battery thereof (T7=T5+T6).

The eighth index value is a rest period (recommended rest period) T8 recommended to the driver of vehicle 1. The greater the fatigue of the driver of vehicle 1 is accumulated, the longer the recommended rest period T8 is calculated to be. Recommended rest period T8 is calculated by, for example, multiplying fatigue level F of the driver of vehicle 1 by a conversion factor Ω (T8=Ω×F). Conversion factor Ω is previously determined by analyzing the data (big data) collected from a large number of vehicles. More specifically, conversion factor Ω can be calculated by multivariate analysis on the relationship between the fatigue level F of the driver before taking a rest, the rest period, and fatigue level F of the driver after taking the rest (i.e., the relationship between the rest period and an amount of recovery of fatigue level F).

FIG. 13 is a flowchart for illustrating more details of the ranking process according to Embodiment 2. Referring to FIGS. 10 and 13, at S331, server 9 extracts chargers the total continuous driving time T3 for which is less than or equal to a given reference time, from among the chargers that are installed within the access range of vehicle 1 (the chargers are narrowed down). This process is the same as process step S231 (see FIG. 8) according to Embodiment 1. However, in some embodiments, the process step S331 may be omitted in Embodiment 2.

When the reference time is, again, 120 minutes in Embodiment 2 as with Embodiment 1, chargers A to D are extracted from among chargers A to E in the example shown in FIG. 10. Charger E the reference time for which is above 120 minutes is placed the lowest (fifth) in the ranking.

At S332, from among the chargers extracted at S331, server 9 further extracts chargers for which the charging completion time T7 of vehicle 1 is greater than or equal to recommended rest period T8.

In the example shown in FIG. 10, chargers A, D the charging completion time T7 for which is greater than or equal to recommended rest period T8, are extracted from among chargers A to D extracted at S331.

At S333, server 9 ranks the chargers the charging completion time T7 for which is greater than or equal to recommended rest period T8, giving the highest priority to a charger for which the difference (T7−T8) between charging completion time T7 and recommended rest period T8 is the least and the lowest priority to a charger for which the difference (T7−T8) between charging completion time T7 and recommended rest period T8 is the greatest. If charging completion time T7 is greater than or equal to recommended rest period T8, it is contemplated that the driver can rest sufficiently. If an excess (T7−T8) of charging completion time T7 relative to recommended rest period T8 is longer than necessary, the driver, even after he/she had sufficient rest, still needs to wait until charging of vehicle 1 is completed. The shorter the excess (T7−T8) of the rest period is, the more promptly the driver can resume driving after resting sufficiently. Thus, the driver convenience can be inhibited from diminishing too much.

In the example shown in FIG. 10, among chargers A, D the charging completion time T7 for which is greater than or equal to recommended rest period T8, charger D for which an excess (T7−T8) of the rest period is less, that is, 10 minutes, is placed first in the ranking, and charger A for which an excess (T7−T8) is greater, that is, 60 minutes, is placed second in the ranking.

Subsequently to the chargers the charging completion time T7 for which is greater than or equal to recommended rest period T8 (the chargers having been ranked at S333), server 9, at S334, ranks the remaining chargers the charging completion time T7 for which is less than recommended rest period T8. Specifically, server 9 ranks the chargers, giving the highest priority to a charger with the least insufficiency (T8−T7) in charging completion time T7 relative to recommended rest period T8 and the lowest priority to a charger with the greatest insufficiency (T8−T7) in charging completion time T7 relative to recommended rest period T8. Stated differently, the chargers that are short of charging completion time T7 relative to recommended rest period T8 are ranked, giving the highest priority to a charger the charging completion time T7 for which is the closest to recommended rest period T8 and the lowest priority to a charger the charging completion time T7 for which is the farthest from recommended rest period T8. Consequently, the driver is allowed to take a rest as close to recommended rest period T8 as possible by selecting a charger that is assigned a higher rank.

In the example shown in FIG. 10, among chargers B, C the charging completion time T7 for which is less than recommended rest period T8, charger C for which an insufficiency (T8−T7) in the rest period is less, that is, 10 minutes, is placed third in the ranking, and charger B for which an insufficiency (T8−T7) in the rest period is greater, that is, 15 minutes, is placed fourth in the ranking.

As described above, letting the driver take a rest sufficiently is prioritized in Embodiment 2, under an idea that the charging time for vehicle 1 can be a rest period for the driver to recover from fatigue. Since chargers the charging completion time T7 for which is greater than or equal to recommended rest period T8 are extracted (S332), the driver can rest sufficiently to recover from fatigue, while vehicle 1 is being charged.

Furthermore, at process step S333, the chargers are ranked, giving the highest priority to a charger with the least excess (T7−T8) of charging completion time T7 relative to recommended rest period T8 and the lowest priority to a charger with the greatest excess (T7−T8) of charging completion time T7 relative to recommended rest period T8. This shortens the wait time since the driver has taken a necessary rest until charging of vehicle 1 is completed, allowing the driver to resume driving promptly. On the other hand, the chargers, the charging completion time T7 for which is insufficient relative to recommended rest period T8, are ranked, giving the highest priority to a charger with the least insufficiency (T8−T7) of charging completion time T7 relative to recommended rest period T8 and the lowest priority to a charger with the greatest insufficiency (T8−T7) of charging completion time T7 relative to recommended rest period T8 (S334). This allows the driver to take a rest as close to recommended rest period T8 as possible, although it is not sufficient, and the driver can recover from fatigue.

Note that the configuration for charging battery 110 with the power supplied external to a vehicle (external charging) is not limited to the configuration of the plug-in charging (contact charging) described above. Battery 110 may be charged according to a non-contact charging method which employs electromagnetic coupling between the vehicle and an external power supply. Specifically, a primary coil is provided on the external power supply side, and a secondary coil is provided on the vehicle side. Utilizing the mutual inductance between the primary coil and the secondary coil, the vehicle is allowed to receive power from the external power supply without contacting it.

Although the present disclosure has been described and illustrated in detail, it is clearly understood that the same is by way of illustration and example only and is not to be taken by way of limitation, the scope of the present disclosure being interpreted by the terms of the appended claims.

What is claimed is:

1. A system comprising:
a server for informing a vehicle of a charger, the vehicle being mounted with a power storage device, and
the vehicle including a first processor that detects a fatigue level of a driver of the vehicle,
the server comprising:
a second processor configured to:
receive, from the vehicle, information indicative of the fatigue level of the driver detected by the first processor; and
when the fatigue level of the driver is above a given reference value,
extract at least one charger installed within an accessible range of the vehicle, based on power stored in the power storage device, a current location of the vehicle, and predetermined usage information for the at least one charger stored in a database, and
inform the vehicle of the extracted charger,
wherein
when a plurality of chargers are extracted, the second processor is configured to rank the extracted chargers, giving a higher rank to a charger of the extracted chargers a continuous driving time for which is below a given reference time than another charger of the extracted chargers the continuous driving time for which is above the reference time, the continuous driving time being a time since the driver starts driving the vehicle until the vehicle arrives at the charger; and
among the extracted chargers, the second processor is configured to rank chargers the continuous driving time for which is above the reference time, giving a highest rank to a charger of the extracted chargers with a shortest wait time and a lowest rank to another charger of the extracted chargers with a longest wait time, the wait time being a time from a time of arrival of the vehicle at the charger until the vehicle is allowed to start charging.

2. The system according to claim 1, wherein
when there are a plurality of chargers the wait time for which is the same, the second processor is configured to rank the plurality of chargers, giving a highest rank to a charger at which a least number of other vehicles are waiting for charging and a lowest rank to a charger at which a greatest number of other vehicles are waiting for charging.

3. The system according to claim 2, wherein
when a plurality of other vehicles are waiting for charging, the second processor is configured to rank the plurality of chargers, giving a highest rank to a charger requiring a shortest driving time by the driver and a lowest rank to a charger requiring a longest driving time by the driver, the driving time being a time taken for the vehicle to arrive at the charger.

4. The system according to claim 1, wherein
when a plurality of chargers are extracted and the fatigue level of the driver is above another reference value higher than the reference value, the second processor is configured to rank the plurality of chargers, giving a highest rank to a charger that is closest to the current location of the vehicle.

5. The system according to claim 1, wherein
when a plurality of chargers are extracted and a given mode is selected by the driver, the second processor is configured to rank the plurality of chargers, giving a highest rank to a charger that is farthest away from the current location of the vehicle.

6. A system comprising:
a server for informing a vehicle of a charger, the vehicle being mounted with a power storage device, and
the vehicle including a first processor that-detects a fatigue level of a driver of the vehicle,
the server comprising:
a second processor configured to:

receive, from the vehicle, information indicative of the fatigue level of the driver detected by the fatigue detection device; and when the fatigue level of the driver is above a given reference value, extract at least one charger installed within an accessible range of the vehicle, based on power stored in the power storage device, a current location of the vehicle, and predetermined usage information for the at least one charger stored in a database, and inform the vehicle of the extracted charger wherein when a plurality of chargers are extracted, the second processor is configured to rank the extracted chargers, wherein the second processor is configured to:

calculate a charging completion time from a time of arrival of the vehicle at a charger until the vehicle completes charging using the charger, and calculate a recommended rest period based on the fatigue level of the driver, the recommended rest period being a rest period during which the driver is recommended to rest while the vehicle is being charged using the charger; and assign a higher rank to a charger of the extracted chargers the charging completion time for which is above the recommended rest period, than another charger of the extracted chargers the charging completion time for which is below the recommended rest period.

7. The system according to claim 6, wherein when there are a plurality of chargers the charging completion time for which is above the recommended rest period, the second processor is configured to rank the plurality of chargers, giving a highest rank to a charger with a least excess of the charging completion time relative to the recommended rest period and a lowest rank to a charger with a greatest excess of charging completion time relative to the recommended rest period.

8. The system according to claim 6, wherein when there are a plurality of chargers the charging completion time for which is below the recommended rest period, the second processor is configured to rank the plurality of chargers, giving a highest rank to a charger with a least insufficiency in the charging completion time relative to the recommended rest period and a lowest rank to a charger with a greatest insufficiency in the charging completion time relative to the recommended rest period.

9. A charger information method for informing, by a server, a vehicle of a charger, the vehicle being mounted with a power storage device, the method comprising:

obtaining, by the server, an accessible range for the vehicle, the accessible range being determined by power stored in the power storage device and a current location of the vehicle;

receiving, by the server, a fatigue level of a driver of the vehicle; and when the fatigue level of the driver is above a given reference value, extracting, by the server, at least one charger installed within the accessible range of the vehicle, based on the power stored in the power storage device, the current location of the vehicle, and predetermined usage information for the at least one charger stored in a database, and informing, by the server, the vehicle of the extracted charger, wherein the method further comprises:

when a plurality of chargers are extracted, ranking the extracted chargers, giving a higher rank to a charger of the extracted chargers a continuous driving time for which is below a given reference time than another charger of the extracted chargers the continuous driving time for which is above the reference time, the continuous driving time being a time since the driver starts driving the vehicle until the vehicle arrives at the charger; and among the extracted chargers, ranking chargers the continuous driving time for which is above the reference time, giving a highest rank to a charger of the extracted chargers with a shortest wait time and a lowest rank to another charger of the extracted chargers with a longest wait time, the wait time being a time from a time of arrival of the vehicle at the charger until the vehicle is allowed to start charging, wherein informing the vehicle of the extracted charger includes transmitting information on the ranked extracted chargers to a navigation system of the vehicle which is configured to show a recommended route to a selected one of the extracted chargers.

* * * * *